United States Patent
Kurosaka et al.

(10) Patent No.: US 10,175,183 B2
(45) Date of Patent: Jan. 8, 2019

(54) AGENT FOR SEARCHING FOR PROTEIN CRYSTALLIZATION CONDITIONS AND METHOD OF SEARCHING FOR PROTEIN CRYSTALLIZATION CONDITIONS

(75) Inventors: Keiichi Kurosaka, Iwaki (JP); Munehiro Kubota, Iwaki (JP); Kengo Sakaguchi, Tsukuba (JP); Keita Ino, Toshima-ku (JP); Itsumi Udagawa, Kasumigaura (JP); Kazuki Iwabata, Matsudo (JP); Yoichi Takakusagi, Noda (JP); Yasutaka Seki, Koshigaya (JP)

(73) Assignees: KUNIMINE INDUSTRIES CO., LTD., Tokyo (JP); TOKYO UNIVERSITY OF SCIENCE EDUCATIONAL FOUNDATION ADMINISTRATIVE ORGANIZATION, Tokyo (JP)

( * ) Notice: Subject to any disclaimer, the term of this patent is extended or adjusted under 35 U.S.C. 154(b) by 788 days.

(21) Appl. No.: 14/000,041

(22) PCT Filed: Mar. 29, 2012

(86) PCT No.: PCT/JP2012/058451
§ 371 (c)(1),
(2), (4) Date: Aug. 16, 2013

(87) PCT Pub. No.: WO2012/133695
PCT Pub. Date: Oct. 4, 2012

(65) Prior Publication Data
US 2013/0344523 A1    Dec. 26, 2013

(30) Foreign Application Priority Data
Mar. 31, 2011   (JP) .................................. 2011-080944

(51) Int. Cl.
*G01N 23/20* (2018.01)
*C07K 1/30* (2006.01)
(Continued)

(52) U.S. Cl.
CPC ............. *G01N 23/20* (2013.01); *C07K 1/306* (2013.01); *C30B 7/00* (2013.01); *C30B 29/58* (2013.01); *C30B 29/54* (2013.01)

(58) Field of Classification Search
CPC ....... C07C 43/043; C07C 41/40; C07C 41/42; B01D 2257/108; B01D 2257/502;
(Continued)

(56) References Cited

U.S. PATENT DOCUMENTS

2006/0194279 A1*   8/2006   Mizukami ............ C07K 1/1133
                                                                    435/69.1

FOREIGN PATENT DOCUMENTS

JP    2005-343766 A    12/2005
JP    2005-343856 A    12/2005
(Continued)

OTHER PUBLICATIONS

Apophyllite alteration in aqueous solutions A nano-scale study of phyllosilicate reactions, Kirill Aldushin, Bochum, 2004.*
(Continued)

*Primary Examiner* — Hua Qi
(74) *Attorney, Agent, or Firm* — Birch, Stewart, Kolasch & Birch, LLP (57) ABSTRACT

An agent for searching for protein crystallization conditions, containing a water-swellable layered silicate having a fluorine atom and a hydroxyl group, wherein the fluorine atom is covalently bonded to the silicate by isomorphous substitution with the hydroxyl group. A method of searching for protein crystallization conditions, which comprises a step of mixing the agent for searching for protein crystallization
(Continued)

conditions described above and a solution in which a protein is dissolved.

12 Claims, 1 Drawing Sheet (51) Int. Cl.
*C30B 7/00* (2006.01)
*C30B 29/58* (2006.01)
*C30B 29/54* (2006.01)

(58) Field of Classification Search
CPC .......... B01D 2257/504; B01D 2257/80; B01D 3/143; B01D 53/1493; C07K 1/306; C30B 29/58; C30B 7/00; G01N 23/20; Y02P 20/152
See application file for complete search history.

(56) References Cited

FOREIGN PATENT DOCUMENTS

| JP | 2005-350294 | A |   | 12/2005 | |
|----|-------------|---|---|---------|---|
| JP | 2005343766  | A | * | 12/2005 | ............... C30B 7/00 |
| JP | 2010-028124 | A |   | 2/2010  | |
| JP | 2011-121789 | A |   | 6/2011  | |

OTHER PUBLICATIONS

Antimicrobial Activities and Cellular Responses to Natural Silicate Clays and Derivatives Modified by Cationic Alkylamine Salts Hsu et al., ACS Applied Materials & Interfaces, vol. 1, No. 11, 2556-2564, 2009.*

Determination of Chemical Formula of a Smectite, M.Onal, Commun. Fac. Sci. Univ. Ank. Series B, V.52 (2). pp. 1-6 (2006).*

Mineral substrates as heterogeneous nucleants in the crystallization of proteins, Paxton et al., Journal of Crystal Growth 198/199 (1999) 656-660.*

Use of layer silicate for protein crystallization: Effects of Micromica and chlorite powders in hanging drops, Takehara et al., Analytical Biochemistry 373 (2008) 322-329.*

Bio-organoclays Based on Phospholipids as Immobilization Hosts for Biological Species, Wicklein et al., Langmuir 2010, 26(7), 5217-5225.*

Ino et al Fluorinated Layered Silicate, PLoS ONE, Jul. 2011, vol. 6, Issue 7, e22582, pp. 1-9.*

Ino et al, The 32nd Annual Meeting of the Molecular Biology Society of Japan, pp. 1-9, 2009.*

Hsu et al., "Antimicrobial Activities and Cellular Responses to Natural Silicate Clays and Derivatives Modified by Cationic Alkylamine Salts", vol. 1, No. 11, 2556-2564, 2009.*

Ino et al., "Heterogeneous Nucleation of Lysozyme Crystal on Fluorinated Layered Silicate", The 32nd Annual Meeting of the Molecular Biology Society of Japan, Year: 2009, p. 1-9.*

Wicklein et al., Bio-organoclays Based on Phospholipids as Immobilization Hosts for Biological Species, Langmuir 2010, 26(7), 5217-5225.*

Extended European Search Report dated Jul. 28, 2014, issued in corresponding European Patent Application No. 12763179.4.

Keita Ino et al; Heterogeous Nucleation of Protein Crystals on Fluorinated Layered Silicate; PLos One; vol. 6; No. 7; Jul. 27, 2011; p. e22582.

European Office Action dated May 3, 2016, issued in European Application No. 12763179.4.

G. Marriner et al., "Apophyllite group: effects of chemical substitutions on dehydration behaviour, recrystallization products and cell parameters", Mineralogical Magazine, Dec. 1990, vol. 54, pp. 567-577.

International Search Report issued in PCT/JP2012/058451 dated Jun. 5, 2012.

Itsumi Utada, Keita Ino et al., "Fussoka Saponite ni yoru Tanpakushitsu Kesshokaku Keisei no Sokushin", Journal of Japanese Biochemical Society, Dec. 9, 2010, 3P-0245.

Keita Ino, and other nine authors, "Promotion of lysozyme crystal nucleation using a fluorine-containing silicate," [online], the 32nd Annual Meeting of the Molecular Biology Society of Japan, Proceedings, 3P-0889, [searched, in Dec. 9, 2009].

McPherson A. et al., "Heterogeneous and epitaxial nucleation of protein crystals on mineral surfaces" Science, 1988, 239, pp. 385-387.

Takehara M. et al., "Use of layer silicate for protein crystallization: Effects of Micromica and chlorite powders in hanging drops", Analytical Biochemistry, 2008, 373, pp. 322-329.

Tang L. et al., "Effects of silanized mica surface on protein crystallization" Acta Crystallographica Section D: Biological Crystallography, 2005, 61, pp. 53-59.

Keita Ino, and other nine authors, "Promotion of lysozyme crystal nucleation using a fluorine-containing silicate," [online], the 32nd Annual Meeting of the Molecular Biology Society of Japan, Proceedings, 3P-0889, [searched, in Dec. 9, 2009], with English translation of abstract.

* cited by examiner

AGENT FOR SEARCHING FOR PROTEIN CRYSTALLIZATION CONDITIONS AND METHOD OF SEARCHING FOR PROTEIN CRYSTALLIZATION CONDITIONS

TECHNICAL FIELD

The present invention relates to an agent for searching for protein crystallization conditions and a method of searching for protein crystallization conditions using the same. More specifically, the present invention relates to an agent for searching for protein crystallization conditions having improved properties of promoting protein crystallization and improved operability, and a method of searching for protein crystallization conditions using the same.

BACKGROUND ART

A technical innovation in a structural biology field has deepened understanding of relationship between a structure of a protein and a function thereof, and has led to development of an innovative drug based on the structure of the protein. In an X-ray crystallographic structure analysis of the protein, crystallization of the protein is an essential step. Crystallization takes place through a process in which a crystal nucleus is formed in a supersaturated solution, and a process in which the crystal nucleus grows to a crystal.

An obstacle to the structural analysis resides in the crystallization step. Upon performing crystallization of a protein of which crystallization conditions are unknown, search for the crystallization conditions first becomes essential. The search for protein crystallization conditions contains a first screening and a second screening. The first screening contains a step of searching for physical conditions and chemical conditions for the purpose of determining conditions, by an extensive search for conditions of crystallization of a target protein, under which the target protein starts crystallization. In this step, for example, protein concentration, kind and a concentration of precipitant, kind of a buffer solution and pH thereof, and the like effective to crystallization are assessed to find out conditions allowing the crystallization to start. On the other hand, the second screening contains a step of searching for elaborated physical conditions and chemical conditions for the purpose of determining final conditions for crystallization of the target protein by modifying the crystallization start conditions selected through the first screening. Modification of the crystallization start conditions in the second screening is performed by partially changing the physical conditions and the chemical conditions constituting the crystallization start conditions or by selectively adding new physical conditions and chemical conditions that are not included in the crystallization start conditions. For example, finally optimum crystallization conditions, specifically, conditions for obtaining a single crystal having a larger possible size with a high quality are found out by finely adjusting conditions such as the concentration of the precipitant and the pH of the buffer solution, or by using an additive or a surfactant that is not used in the first screening, and also by finely adjusting the kind, the concentration or the like thereof. In any of these screenings, a trial-and-error examination of conditions is required for a limitless number of combinations of physical conditions and chemical conditions according to the target protein. For example, the second screening is performed through many kinds of examinations for conditions, such as kind of precipitant, pH of a solution, concentration of a protein solution, and temperature thereof. Crystals obtained after determining the crystallization conditions are subjected to a structural analysis by X-ray irradiation. Before irradiation with X-rays, the crystals may be occasionally immersed into an antifreeze containing a cryoprotectant. Moreover, when omission of the immersion step is desired, protein crystallization is tried using a precipitant solution containing the cryoprotectant in the first screening or the second screening. In any case, each screening is repeated until a desired crystal is obtained.

However, a protein is not generally active in forming crystal nuclei, and therefore hard to cause crystallization. In addition thereto, conditions of crystallization of a new protein cannot be anticipated at all, and new crystallization conditions cannot be anticipated even to a protein in which crystallization conditions are known, either. Under such a situation, the conventional first screening sometimes did not result in formation of crystals or even crystalline precipitates, and could not determine crystallization start conditions. Depending on the protein crystallization conditions, presence or absence of crystal nucleation is changed by a slight change of setting conditions, such as a solvent and temperature. Therefore, the conventional second screening that is the modification of the crystallization start conditions as selected in the first screening sometimes yielded no crystal. Control of protein crystal nucleation by the modification of setting conditions such as the solvent or the temperature is difficult. Therefore, the conventional second screening inclined to result in no crystal formation at a desired size and in the number of pieces. Moreover, the conventional second screening resulted in no crystal formation under conditions referred to as a metastable region in which supersaturation conditions are less than the crystallization start conditions, and in which no crystal nucleation takes place but crystal growth potentially takes place. When protein crystals are formed in the metastable region, the crystal inclines to have a sufficiently high quality, as is well known in the art. The cryoprotectant suppresses the protein crystal nucleation. Therefore, use of a reagent containing the cryoprotectant in the first screening and the second screening inclined to cause no protein crystallization. As described above, the conventional screening system inclined to yield no objective crystals or waste the protein being a precious sample after all even with an examination of conditions in which a load is high. Accordingly, a development has been required for a simple, economical and highly reliable method for searching for protein crystallization conditions.

In response thereto, an attempt was proposed for improving efficiency of protein crystallization by using a layered silicate. Patent Literature 1 discloses a screening chip for searching for protein crystallization conditions by using a layered silicate, in which the silicate is applied in the form of a film onto a support. However, the layered silicate described in Patent Literature 1 has a problem of not sufficiently promoting crystal nucleation of extensive proteins in screening on the assumption of searching for conditions of crystallization of various proteins. Moreover, the film is not a thin uniform film, and therefore is likely to be easily detached. Furthermore, the invention described in Patent Literature 1 requires a user of the screening chip to select an optimum type of the layered silicate and an amount of layered silicate application. Such an examination of conditions causes consumption of a large amount of protein solution. Moreover, the silicate is present in a part in which the screening chip and the protein solution are not in contact with each other. Therefore, extensive penetration of the protein solution inclines to decrease a degree of supersaturation and to cause protein denaturation.

Patent Literatures 2 and 3 disclose an agent for controlling protein crystal formation by using a layered silicate, and a method for controlling the formation using the same. However, the layered silicates described in Patent Literatures 2 and 3 also promotes only insufficient protein crystal nucleation in screening in a manner similar to the layered silicate described in Patent Literature 1. Moreover, the layered silicate described in Patent Literatures 2 and 3 has a weak surface negative charge and low water-swelling properties. Therefore, the layered silicate inclines to agglomerate and precipitate when the layered silica comes in contact with a screening reagent containing a precipitant at a high concentration.

Non-Patent Literature 1 discloses an agent for controlling lysozyme crystal formation containing a fluorine-containing layered silicate. Non-Patent Literature 1 discloses use of the layered silicate in lysozyme crystallization. However, no description is made on use of the layered silicate on the assumption of searching for conditions of crystallization of various proteins. Moreover, the layered silicate described in Non-Patent Literature 1 also insufficiently promotes the crystal nucleation of the protein in screening.

Non-Patent Literature 2 discloses an agent for controlling protein crystal formation that contains fluorine mica. This fluorine mica is synthesized by a solid-state reaction process, by using talc as a starting material, in the absence of moisture. However, the fluorine mica described in Non-Patent Literature 2 has no hydroxyl group. Therefore, crystal nucleation rate cannot be adjusted, and crystal nucleation is not promoted in some cases. Therefore, the fluorine mica is insufficient for an agent for searching for crystallization conditions. Moreover, the fluorine mica is non-swelling in water, and therefore inclines to agglomerate or precipitate in contact with a reagent containing a precipitant at a high concentration. Accordingly, use of the fluorine mica for a dispersion liquid needs agitation for uniformly dispersing the fluorine mica.

Non-Patent Literature 3 discloses an agent for controlling protein crystal formation that contains a mineral containing a layered silicate. The layered silicate constituting the mineral described in Non-Patent Literature 3 promotes protein crystal nucleation only insufficiently.

Non-Patent Literature 4 discloses an agent for controlling protein crystal formation that contains mica having an amino group. The mica described in Non-Patent Literature 4 forms a sheet-like material to be used for sealing the well in a hanging-drop process. This sheet-like material promotes protein crystal nucleation only insufficiently.

CITATION LIST

Patent Literatures

Patent Literature 1: JP-A-2005-350294 ("JP-A" means unexamined published Japanese patent application)
Patent Literature 2: JP-A-2005-343856
Patent Literature 3: JP-A-2005-343766

Non-Patent Literatures

Non-Patent Literature 1: Keita Ino, and other nine authors, "Promotion of lysozyme crystal nucleation using a fluorine-containing silicate," [online], the 32nd Annual Meeting of the Molecular Biology Society of Japan, Proceedings, 3P-0889, [searched, in Dec. 9, 2009]
Non-Patent Literature 2: Takehara M. et al., "Use of layer silicate for protein crystallization: Effects of Micromica and chlorite powders in hanging drops", Analytical Biochemistry, 2008, 373, p. 322-329
Non-Patent Literature 3: McPherson A. et al., "Heterogeneous and epitaxial nucleation of protein crystals on mineral surfaces" Science, 1988, 239, p. 385-387
Non-Patent Literature 4: Tang L. Et al., "Effects of silanized mica surface on protein crystallization" Acta Crystallographica Section D: Biological Crystallography, 2005, 61, p. 53-59

SUMMARY OF INVENTION

Technical Problem

The present invention involves searching for protein crystallization conditions and has a task of providing an agent for searching for protein crystallization conditions having an improved property of promoting protein crystal formation and an improved operability. Further, the present invention provides a method of searching for protein crystallization conditions.

Solution to Problem

In view of such a circumstance, the present inventors diligently conducted research. As a result, the present inventors created an agent to search protein crystallization conditions that contains a water-swellable layered silicate having a fluorine atom and a hydroxyl group, in which the fluorine atom is covalently bonded to the silicate by isomorphous substitution with the hydroxyl group. More specifically, the present inventors found that a molar percent of the fluorine atom to the hydroxyl group of the layered silicate relates to the protein crystal formation, and can control the crystal formation rate and the probability of the crystal formation. According to the present invention, the present inventors found that a protein can be crystallized even under conditions in which the protein could not be sufficiently crystallized so far. Furthermore, the present inventors found that a strong surface negative charge of the water-swellable layered silicate having the fluorine atom, and excellent water-swelling properties thereof contribute to improvement in operability of the agent for searching for protein crystallization conditions. The present inventors further diligently conducted research based on these findings, and thus achieved the present invention.

That is, the present invention provides an agent for searching for protein crystallization conditions, containing a water-swellable layered silicate having a fluorine atom and a hydroxyl group, wherein the fluorine atom is covalently bonded to the silicate by isomorphous substitution with the hydroxyl group.

Further, the present invention provides a method of searching for protein crystallization conditions, containing a step of mixing the agent for searching for protein crystallization conditions described above, and a solution in which a protein is dissolved.

Further, the present invention provides use of the agent for searching for protein crystallization conditions described above, wherein the agent for searching for protein crystallization conditions described above is mixed with a solution in which a protein is dissolved, to recover crystallized proteins.

In the present invention, the term "search(ing) for protein crystallization conditions" means setting physical conditions and chemical conditions in order to search for conditions of crystallization of a target protein, and determining physical conditions and chemical conditions suitable for crystallization of the target protein by using as criteria of judgment presence or absence of crystal formation, presence or absence of crystalline precipitate formation, presence or absence of noncrystalline precipitate formation, a success rate of crystallization, crystallization time of formed crystals, a shape or a size of formed crystals, crystal nucleus density (the number of crystals per unit area), or X-ray diffraction data.

Advantageous Effects of Invention

According to the agent for searching for protein crystallization conditions of the present invention, it is possible to carry out an efficient and practical search for the crystallization conditions by an examination of conditions in which a load is relatively low.

Moreover, according to the method for searching for protein crystallization conditions of the present invention, it is possible to carry out efficient and practical setting of conditions suitable for protein crystallization in a step in which a load is relatively low.

BRIEF DESCRIPTION OF THE DRAWINGS

In FIG. 1, (a) shows an X-ray diffraction pattern of the saponite in Preparation Example 1, (b) shows an X-ray diffraction pattern of the saponite in Preparation Example 2, and (c) shows an X-ray diffraction pattern of the saponite in Preparation Example 3.

In FIG. 2, (a) shows an isotherm of the saponite in Preparation Example 1, (b) shows an isotherm of the saponite in Preparation Example 2, and (c) shows an isotherm of the saponite in Preparation Example 3.

MODE FOR CARRYING OUT THE INVENTION

The present description is summarized in the form of claims specifying and explicitly claiming subject matters of the present invention, and will be better understood from the following explanations relating to an embodiment. The present invention is advantageous in all agents for controlling protein crystal formation as designed to crystallize a protein, and in relation to a drawing attached to the present invention, is disclosed as a preferred embodiment of an agent for searching for crystallization conditions for searching for protein crystallization conditions. Furthermore, other features and advantages according to the present invention are clear from the following explanations of an embodiment, appropriately with referring to attached drawings, and claims.

The term "screening" used in the present specification means a step for setting physical conditions and chemical conditions in order to search for conditions of crystallization of an object, and determining physical conditions and chemical conditions suitable for crystallization of the object by using as criteria of judgment presence or absence of crystal formation, presence or absence of crystalline precipitate formation, presence or absence of noncrystalline precipitate formation, a success rate of crystallization, crystallization time of formed crystals, a shape or a size of formed crystals, crystal nucleus density, or X-ray diffraction data.

The term "metastable region" used in the present specification means a set of supersaturation conditions in which crystal nucleation of an object does not take place but crystal growth potentially takes place.

The term "layered silicate" used in the present specification means a compound having a two-dimensional layered structure, in which the layered structure is constituted of at least a silicon atom and an electrically negative ligand. The layered silicate may have a single layer of a tetrahedron layer and/or an octahedron layer, or a mixed layer of these layers. A tetrahedron sheet takes a structure in which four oxygen ions ($O^{2-}$) surround a silicon ion ($Si^{4+}$) or an aluminum ion ($Al^{3+}$), three vertices are shared with adjacent tetrahedrons, and the resultant structure constitutes a hexagonal network, and is connected in a sheet form. An octahedron sheet has a two-dimensionally spread structure in which octahedrons formed by six oxygen ions ($O^{2-}$) or hydroxide ions ($OH^-$) surrounding a magnesium ion ($Mg^{2+}$) or aluminum ion share edges. When the tetrahedron sheet and the octahedron sheet are combined, the oxygen ions at the vertices of the tetrahedron sheet are shared. Moreover, the hydroxide ion may be occasionally isomorphously substituted by a fluorine ion ($F^-$).

The term "isomorphous substitution" used in the present specification means a reaction in which a certain atom constituting a certain compound having a crystal structure is replaced by any other atom having an ion radius identical or similar with an ionic radius of the certain atom without changing the crystal structure of the compound.

The agent for searching for protein crystallization conditions according to the present invention (hereinafter, also referred to simply as "agent for searching for crystallization conditions") contains a water-swellable layered silicate having a fluorine atom and a hydroxyl group at a specific ratio. The fluorine atom is covalently bonded to the layered silicate by isomorphous substitution. The layered silicate, when the layered silicate is brought into contact with a protein, forms an aggregate of the protein functioning as a crystal nucleus. The layered structure, the fluorine atom, and the hydroxyl group of the layered silicate can promote the protein crystal nucleation. The fluorine atom and the water-swelling properties of the layered silicate provide the agent for searching for crystallization conditions with a uniform dispersibility and film-forming properties. The agent for searching for crystallization conditions according to the present invention is suitable for searching for crystallization conditions for crystallization of a protein in an amount from a nanogram unit to a microgram unit.

The agent for searching for crystallization conditions may be constituted of the layered silicate only, or a mixture of the layered silicate and any other component. Specific examples of the other component include pure water, a precipitant, a buffering agent, an additive, an organic solvent, and a mixed component of these components. The agent for searching for crystallization conditions may contain a single or a plurality of layered silicates.

The layered silicate used for the agent for searching for crystallization conditions according to the present invention is not particularly limited. Preferred examples thereof include montmorillonite, talc, phlogopite, mica, kaolin, chlorite, pyrophyllite, vermiculite, endellite, chrysotile, beidellite, halloysite, nontronite, sericite, dickite, antigorite, hectorite (fluorine hectorite), sauconite, kanemite, makatite, octosilicate, magadiite, kenyaite, stevensite and saponite. More preferred examples include mica, montmorillonite, stevensite, hectorite and saponite; and particularly preferred examples include saponite.

Specific examples of the layered silicate include a natural product or a synthetic product. The natural product may contain an impurity. However, the impurity is preferably removed from a viewpoint of stringent control of crystallization in nucleation. The synthetic product is highly pure, in which isomorphous substitution efficiency thereof can be freely controlled during synthesis. Accordingly, stringent control in nucleation is allowed.

The layered silicate may have an arbitrary mean particle diameter. The mean particle diameter is preferably 2 to 50 μm from a viewpoint of uniform dispersibility. The mean particle diameter may be determined by measurement of a laser-type particle size distribution using water as a dispersion medium.

The layered silicate may have arbitrary cation exchange capacity. The cation exchange capacity is preferably at least 10 meq/100 g, and further preferably at least 60 meq/100 g. The cation exchange capacity in a suitable range provides the layered silicate with a negative charge suitable for nucleation promotion.

A specific surface area of the layered silicate is preferably from 1 to 1,000 $m^2/g$, more preferably from 10 to 500 $m^2/g$, and further preferably from 100 to 200 $m^2/g$. The specific surface area provides the layered silicate with surface charge density suitable for nucleation promotion.

The layered silicate has water-swelling properties, and therefore is hard to cause spontaneous precipitation in a reagent containing a precipitant at a high concentration. Accordingly, such a layered silicate allows provision of a dispersion liquid type agent that is used for searching for crystallization conditions, and has improved uniform dispersibility, long-term stability of a uniform dispersion state, and redispersibility. Moreover, the water-swellable layered silicate has excellent film-forming properties. Therefore, such a layered silicate allows provision of a uniform and thin film-like agent for searching for crystallization conditions.

The layered silicate is preferably of a smectite group. The smectite group has a 2:1 layered structure. Use of the smectite group allows provision of an agent for searching for crystallization conditions that has improved uniformity and operability.

The layered silicate is further preferably saponite, among the smectite group. Saponite has a layered structure in which a silicon atom in a tetrahedron layer is replaced by an aluminum atom, and therefore has a permanent negative charge.

Saponite provides the agent for searching for crystallization conditions with properties for nucleation promotion resulting from a mesopore. Use of saponite allows promotion of further diversified protein crystal nucleation in the form of a single product, and allows provision of improved uniformity and operability for the agent for searching for crystallization conditions.

With regard to the layered silicate, any bonding form is allowed to the hydroxyl group. For example, the layered silicate may have the hydroxyl group bonded in the form of a covalent bond. Alternatively, the layered silicate may have a hydroxyl group-containing compound directly or indirectly bonded thereto.

In a preferred embodiment, the hydroxyl group is covalently bonded in a crystal structure of the layered silicate. The layered silicate having the fluorine atom and the hydroxyl group adsorbs a protein in a protein solution, and forms protein aggregates functioning as a crystal nucleus. Moreover, a molar percent of each of the fluorine atom and the hydroxyl group can be controlled by an amount of addition of a charged fluorine raw material during synthesis.

The fluorine atom is covalently bonded in the crystal structure of the layered silicate by isomorphous substitution. Moreover, the layered silicate formed by isomorphous substitution of the fluorine atom has a relatively large cation exchange capacity. Therefore, such a layered silicate increases a surface charge density of the layered silicate. Accordingly, the layered silicate into which the fluorine atom is introduced by isomorphous substitution adsorbs a protein with a high density in a protein solution to effectively form protein aggregates functioning as the crystal nucleus.

Moreover, the permanent negative charge of the layered silicate further increases by allowing isomorphous substitution of the fluorine atom, in comparison with the charge of the layered silicate without isomorphous substitution, to allow a strong electrostatic repulsion to act between particles of the layered silicate. Accordingly, the agent for searching for crystallization conditions is hard to aggregate even in contact with the reagent containing a precipitant at a high concentration, and has improved uniformity.

The layered silicate having the fluorine atom and the hydroxyl group can be synthesized by an ordinary method. Specific examples of the synthetic method include a hydrothermal synthetic process, a fusion synthetic process, a high-pressure synthetic process, a solid-state reaction process, a flame fusion process, and a transformation process. Among these, a hydrothermal synthesis using a fluorine source is preferred. The hydrothermal synthesis using a fluorine source easily allows introduction of the fluorine atom and the hydroxyl group into a product by isomorphous substitution. Moreover, the layered silicate having the fluorine atom and the hydroxyl group may be synthesized by a high-pressure synthetic process, a solid-state reaction process, a flame fusion process or a transformation process, each using a fluorine source. Furthermore, the layered silicate having the fluorine atom and the hydroxyl group may be synthesized by introducing a hydroxyl group into fluorine-containing layered silicate.

A molar percent of the fluorine atom to the hydroxyl group in the layered silicate influences a success rate of protein crystallization, a rate of crystallization, crystal nucleus density, and a size of crystals. In particular, a positive correlation is present between the molar percent of the fluorine and a frequency of nucleation, and a negative correlation is present between the molar percent of the fluorine atom and the size of crystals. The fluorine content and the molar percent of the fluorine atom to the hydroxyl group may be quantitatively determined and calculated by means of an X-ray fluorescence system (RIX 1000, manufactured by Rigaku Corporation) by using layered silicate from which free fluorine and a soluble ion are washed and removed by dispersing a synthesized sample into distilled water, and then performing filtration or centrifugation several times.

In a preferred embodiment, a molar percent of the fluorine atom for the total of the fluorine atom and the hydroxyl group in the layered silicate is preferably from 3% to 15%, further preferably from 4% to 12%, and most preferably from 5 to 10%. Moreover, a molar percent of the hydroxyl group is preferably from 85% to 97%, further preferably from 88% to 96%, and most preferably from 90% to 95%. In this range, the layered silicate has a nucleation promotion effect, and therefore allows improvement in the success rate of crystallization in the first screening using the agent for searching for crystallization conditions. Moreover, the success rate of crystallization, the rate of crystal formation, the size of crystals, and the crystal nucleus density can be controlled by appropriately adjusting the molar percents. If the molar percent of the fluorine atom in the agent for searching for crystallization conditions is too low (the molar percent of the hydroxyl group is too high), the layered silicate does not effectively promote crystal nucleation, and therefore desired crystals cannot be occasionally obtained in the first screening and the second screening. Moreover, if the molar percent of the fluorine atom is too high (the molar percent of the hydroxyl group is too low), the size of crystals occasionally becomes small or high-quality crystals for X-ray diffraction or the like cannot be occasionally obtained. Herein, when the crystallization start conditions selected through the first screening using the agent for searching for crystallization conditions according to the present invention already allows formation of desired protein crystals, the second screening may be skipped. Moreover, when the crystallization start conditions are already found out, the agent for searching for crystallization conditions according to the present invention may be applied only to the second screening.

The agent for searching for crystallization conditions may contain a layered inorganic compound other than the layered silicate. Specific examples of the layered inorganic compound include a layered metal hydroxide and a layered complex hydroxide.

The agent for searching for crystallization conditions may contain an arbitrary agent for controlling protein crystal formation. Preferred examples of the agent for controlling crystal formation are disclosed in JP-A-2007-55931, WO 2004/041847, WO 02/088435 and JP-A-8-294601. These preferred examples of the agent for controlling crystal formation are incorporated herein by reference.

The agent for searching for crystallization conditions may contain an arbitrary precipitant for decreasing solubility of a protein. Specific examples of the precipitant include a salt, a water-soluble polymer compound, an organic solvent, and a mixed component of these substances.

Specific examples of the salt include ammonium sulfate, magnesium sulfate, sodium sulfate, lithium chloride, sodium chloride, potassium chloride, magnesium chloride, calcium chloride, sodium nitrate, sodium fluoride, sodium tartrate, sodium formate, ammonium phosphate, lithium sulfate, cobalt chloride, zinc sulfate, and sodium malonate.

Specific examples of the water-soluble polymer compound include polyethylene glycol, polyethylene glycol monoalkyl ether, and polyethyleneimine, each having a molecular weight of from 400 to 20,000.

Specific examples of the organic solvent include ethanol, methanol, acetone, 2-methyl-2,4-pentanediol, isopropanol, butanol, dioxane, dimethylsulfoxide and dimethylformamide.

The agent for searching for crystallization conditions may contain a surfactant. Specific examples of the surfactant include dodecyl sodium sulfate, dodecyl lithium sulfate, dodecyldimethylamine-N-oxide, N-decyl-β-D-maltoside, N-dodecyl-β-D-maltopyranoside, N-octyl-β-D-glucopyranoside, N-octyl-β-D-thioglucopyranoside, N-nonyl-β-D-thiomaltoside, polyoxyethylene-octylphenyl ether, decanoyl-N-methylglucamide and sucrose monolaurate.

The agent for searching for crystallization conditions may contain a cryoprotectant. Specific examples of the cryoprotectant include glycerol, ethylene glycol, sucrose and trehalose.

The agent for searching for crystallization conditions may contain an arbitrary additive. Specific examples of the additive include a ligand, an inhibitor, a coenzyme, a substrate, an amino acid, a gel, an antibody, and a mixture of these additives. Preferred examples of the amino acid are disclosed in WO 2008/102469. Further, preferred examples of the gel are disclosed in JP-A-2007-45668. These preferred examples of the amino acid and the gel are incorporated herein by reference.

The agent for searching for crystallization conditions may contain an ionic liquid within the range in which protein crystallization is not adversely affected. Preferred examples of the ionic liquid are described in Russell A. Judge et al., "The Effect of Ionic Liquids on Protein Crystallization and X-ray Diffraction Resolution", CRYSTAL GROWTH & DESIGN, 2009, Vol. 9, No. 8, p. 3463-3469. These preferred examples of the ionic liquid are incorporated herein by reference.

The agent for searching for crystallization conditions may contain an arbitrary reagent. Preferred examples of the reagent are disclosed in JP-A-2006-83126. These preferred examples of the reagent are incorporated herein by reference.

The agent for searching for crystallization conditions may have any dosage form. Specific examples include a solid agent, a dispersion liquid agent, and a clay-like semi-solid agent. In a preferred embodiment, the agent for searching for crystallization conditions includes a dispersion liquid agent prepared by adding powder layered silicate to a dispersion medium, or a thin film-like solid agent prepared by applying layered silicate onto a support. A dispersion liquid agent of water-swellable layered silicate having the fluorine atom is hard to aggregate and precipitate in a reagent containing a precipitant or the like at a high concentration. The thin film-like solid agent allows improvement in operability in searching for crystallization conditions because preparation of a dispersion liquid is unnecessary.

Any support may be used for carrying the thin film-like solid agent. Preferred examples thereof include a cover glass, a slide glass, a plate, a bridge, or a rod. Among these, a bridge is particularly preferable. A thin film-like solid agent applied to the bridge allows rapid search for crystallization conditions by a sitting-drop vapor diffusion process.

An ordinary dispersion medium can be used for the agent for searching for crystallization conditions. Specific examples of the dispersion medium include pure water, a buffer solution, a precipitant solution, a surfactant solution, an alcohol, an organic solvent, a chelating agent solution, a reducing agent solution, a cryoprotectant solution, an ionic liquid, a mineral oil, and a mixed solvent of these media.

In a preferred embodiment, the dispersion medium is an aqueous solution of a nonionic water-soluble polymer compound. Specific examples of the nonionic water-soluble polymer compound include polyethylene glycol and polyethylene glycol monoalkyl ether. Use of this dispersion medium allows effective prevention of aggregation and precipitation of layered silicate particles, and fractionation of a uniform dispersion liquid without agitation.

Accordingly, the use of the dispersion medium allows execution of an efficient search for crystallization conditions not only by a manual operation but also by a combination with a known crystallization automated apparatus having no agitation apparatus. Preferred examples of the automated apparatus are disclosed in JP-A-2010-151821, JP-A-2006-281139, JP-A-2003-14596, JP-A-2004-194647 and JP-T-2003-502652 ("JP-T" means searched and published International patent application). These preferred examples of the automated apparatuses are incorporated herein by reference.

In another preferred embodiment, the agent for searching for crystallization conditions is in the form of the solid agent. Specific examples of the solid agent include powder, granules, a thick film, a thin film, a tablet, and a freezedrying agent. The thick film-like or thin film-like solid agent may be a free-supporting film, or a film carried on a support. The thick film-like or thin film-like agent for searching for crystallization conditions has improved operability because no agitation is necessary at all. Furthermore, the thick film-like or thin film-like agent for searching for crystallization conditions has improved uniformity due to absence of foam formation even when a surfactant-containing reagent is used. Accordingly, the thick film-like or thin film-like agent for searching for crystallization conditions is suitable for high-throughput screening in a large scale.

The thick film-like or thin film-like solid agent may be formed by an arbitrary film-forming method. Preferred examples of the film-forming method are disclosed in JP-A-2008-119659, JP-A-2008-18299, JP-A-2006-150160, JP-A-2005-163058 and JP-A-2001-220244. These preferred examples of the film-forming method are incorporated herein by reference.

In a further preferred embodiment, the agent for searching for crystallization conditions is a thin film-like solid agent applied onto the support. The thin film-like solid agent is not only prevented from easily detaching from the support because an application surface of the layered silicate has no unevenness, but also allows stringent control of crystal nucleation. The thin film-like solid agent has further improved uniformity and operability. The thin film is preferably formed only on a part in contact with the protein on the support. This constitution allows not only reduction of an amount of layered silicate to be used, but also prevention of excessive waste of the protein and a rapid decrease of moisture by extensive penetration of the protein solution.

In a still further preferred embodiment, the support is a cover glass, a slide glass, a plate, a bridge, or a rod. Preferred examples of the support are disclosed in JP-A-2002-179500, JP-A-2002-233702, JP-T-2006-500960, U.S. Pat. No. 5,419,278 and U.S. Pat. No. 5,096,676. These preferred examples of the support are incorporated herein by reference. This constitution allows execution of efficient screening not only by a manual operation but also by a combination with a known crystallization automated apparatus having no agitation apparatus.

Kinds of proteins to which the agent for searching for crystallization conditions is applied are not particularly limited. Specific examples of the protein include an acidic protein, a basic protein, a neutral protein, a glycoprotein, a lipoprotein, a membrane protein, an enzyme, an antibody, an acceptor, a transcription factor, an oligopeptide, a polypeptide, a complex of proteins, a complex of a protein and a nucleic acid, a complex of a protein and a low-molecular-weight compound, a complex of a protein and a coenzyme, a complex of a protein and saccharides, a complex of a protein and a metal, and a complex of an enzyme and a substrate. Among these, an acidic protein, a basic protein, and a neutral protein are preferable. These proteins may have an arbitrary molecular weight and isoelectric point.

The protein may be soluble or insoluble in pure water or a buffer solution. The insoluble protein may be dissolved by using an arbitrary solubilizing agent. Preferred examples of the solubilizing agent are disclosed in JP-A-2007-314526, JP-T-2001-519836, JP-A-5-125092 and JP-A-5-32689. These preferred examples of the solubilizing agent are incorporated herein by reference.

The protein may be natural or artificial. The protein may be artificial as synthesized by various methods. Specific examples of the artificial protein include an expressed protein synthesized by a gene recombination technology, a protein synthesized by a chemical synthetic process, and a protein synthesized by a fermentation process. The expressed protein may be synthesized using an arbitrary expression system. Specific examples of the expression system include an *Escherichia coli* expression system, a yeast expression system, an insect cell expression system, a mammalian cell expression system, and a non-cell expression system. Preferred examples of the expression system are disclosed in JP-A-2010-63386, JP-A-2010-11851, JP-A-2008-193953, JP-T-2008-538503, JP-T-2007-501007, JP-T-2006-502691, JP-T-2006-508684, JP-T-2005-517385, JP-T-2004-506428 and JP-T-2003-511067. These preferred examples of the expression system are incorporated herein by reference.

The expressed protein may be prepared by appropriately fusing a tag protein. Preferred examples of the tag protein are disclosed in JP-A-2010-75090, JP-T-2004-532025, JP-A-2003-289882 and JP-A-2003-38195. These preferred examples of the tag protein are incorporated herein by reference.

The solvent for dissolving the protein is not particularly limited. Specific examples of the solvent for dissolving the protein include pure water, a buffer solution, a precipitant solution, a surfactant solution, an alcohol solution, an organic solvent, a chelating agent solution, a reducing agent solution, a cryoprotectant solution, an ionic liquid, and a mixed solution of these solvents. The solvent for dissolution is preferably a buffer solution. Specific examples of buffer components include sodium acetate, sodium phosphate, sodium citrate, sodium cacodylate, sodium carbonate, imidazole, tris(hydroxymethyl)aminomethane, Good buffers, and a mixed component of these components. The buffer solution may have arbitrary pH, for example, in the range of from pH 3.5 to pH 10.0.

The method of searching for crystallization conditions according to the present invention includes a step of mixing the agent for searching for crystallization conditions that contains the water-swellable layered silicate having the fluorine atom and the hydroxyl group, and a solution in which a protein is dissolved.

The concentration of the protein solution is not particularly limited, as long as the protein is dissolved therein. From a viewpoint of effectively promoting crystallization, an initial protein concentration is preferably high, and the concentration is preferably 2 mg/mL or more, more preferably from 5 mg/mL to 200 mg/mL, and particularly preferably a concentration in a vicinity of saturation solubility.

An amount of addition of the agent for searching for crystallization conditions to the protein solution is not particularly limited, but a final concentration of the layered silicate in the protein solution is adjusted to be preferably at least 0.01% (w/v) or more, and more preferably from 0.01% to 1.0% (w/v). In order to achieve a high nucleation frequency, the final concentration of the layered silicate is adjusted to be preferably from 0.01% to 0.5% (w/v), more preferably from 0.05% to 0.3% (w/v), and still further preferably from 0.1% to 0.2% (w/v).

A technique for crystallizing the protein is not particularly limited. Specific examples of the crystallization method include a batch process, a vapor diffusion process, dialysis, a free interface diffusion process, a concentration process, a light irradiation process, a vibration process, and an agitation process. As the vapor diffusion process, a hanging-drop process, a sitting-drop process, or a sandwich-drop process are suitably applied. The vapor diffusion process allows easy and rapid screening using a trace amount of protein. Preferred examples of the crystallization method are disclosed in JP-A-2010-13420, JP-A-2010-1220, JP-A-2003-306497, Japanese Patent No. 4029987 and JP-A-6-116098. These preferred examples of the crystallization method are incorporated herein by reference.

The protein may be crystallized by using an arbitrary vessel. Preferred examples of the vessel are disclosed in JP-A-2009-172530, JP-A-2008-309617, JP-A-2008-126135, JP-A-2007-1788, JP-A-2006-124238, JP-A-2006-308607, JP-T-2005-502571, JP-T-2005-515151, JP-T-2006-525864, JP-A-2004-307335, JP-A-2003-248004, JP-T-2002-528701, JP-T-2002-536255, JP-A-11-130600, U.S. Pat. No. 5,096,676, U.S. Pat. No. 5,130,105, U.S. Pat. No. 5,221,410 and WO 01/088231. These preferred examples of the vessel are incorporated herein by reference.

The protein may be crystallized under arbitrary temperature conditions. The temperature is preferably from 4° C. to 37° C., and further preferably from 4° C. to 20° C.

Formed crystals may be observed using a microscope. Specific examples of the microscope include a stereoscopic microscope, an optical microscope, a polarizing microscope, and an electron microscope. Moreover, the crystals may be observed with the naked eye or by using an apparatus for crystal detection. Preferred examples of the apparatus for crystal detection are disclosed in JP-A-2007-45663, JP-A-2005-9949, JP-A-2006-242690, JP-A-2004-323336 and JP-A-2007-248280. These preferred examples of the apparatus for crystal detection are incorporated herein by reference.

The formed crystals may be analyzed by means of an X-ray diffractometer. X-ray diffraction can be performed regardless of presence or absence of adhesion of the agent for searching for crystallization conditions to the crystals. The agent for searching for crystallization conditions according to the present invention does not adversely affect an X-ray diffraction experiment, and a good X-ray diffraction pattern can be obtained even by using the crystals to which the agent for searching for crystallization conditions adheres.

The formed crystals may be used as seed crystals for searching for new crystallization conditions.

Moreover, the agent for searching for crystallization conditions according to the present invention may be used as an agent for controlling protein crystal formation or an agent for promoting protein crystal formation. Furthermore, the agent for searching for crystallization conditions according to the present invention may be applied to industrial protein purification applying protein crystallization, or to crystallization of a biopolymer other than the protein. These applications include a case where the agent for searching for crystallization conditions according to the present invention is allowed to act as a nucleating agent or an agent for crystal nucleation.

EXAMPLES

Hereinafter, the present invention is explained in more detail based on Preparation Examples, Testing Examples, and Comparative Testing Examples, but the present invention is not limited to these Examples without departing from the spirit of the present invention.

Preparation Example 1

Based on theoretical chemical formula of Na-type saponite $Na_{0.33}(Mg_3)(Al_{0.33}Si_{367})O_{10}(OH)_2$, 1.5 L of hydrated gel was prepared by reacting water glass (manufactured by Hokuetsu Kagaku Kogyo Kabushiki Kaisha), magnesium sulfate (manufactured by Kanto Chemical Co., Inc.) and aluminum sulfate (manufactured by Kanto Chemical Co., Inc.) with each other to be Si:Mg:Al=3.67:3:0.33 in molar percents. Then, 2 L of reaction gel was prepared by adding 0.5 L of aqueous solution prepared by dissolving sodium fluoride (manufactured by Kanto Chemical Co., Inc.) into this hydrated gel. The reaction gel was put into a 3L-autoclave vessel, and a hydrothermal synthesis was performed at 250° C. for 4 hours. The thus-obtained product (1 L) after the hydrothermal synthesis was subjected to suction filtration using a filter paper, and moisture was removed. To the resultant cake, 2 L of water was added to be redispersed by agitation, and the resultant product was filtrated again. Unconverted reactants were washed and removed by repeating a redispersion and re-filtration operation three times. The resultant cake was dried, and thus synthetic saponite having a fluorine atom and a hydroxyl group (hereinafter, occasionally referred to as "saponite in Preparation Example 1") was obtained.

Preparation Example 2

Synthetic saponite having a fluorine atom and a hydroxyl group (hereinafter, occasionally referred to as "saponite in Preparation Example 2") was obtained in the same manner as in Preparation Example 1, except that the amount of sodium fluoride formulation in Preparation Example 1 was changed.

Preparation Example 3

Synthetic saponite having a hydroxyl group (hereinafter, occasionally referred to as "saponite in Preparation Example 3") was obtained in the same manner as in Preparation Example 1, except that sodium hydroxide (manufactured by Kanto Chemical Co., Inc.) was formulated in place of the sodium fluoride in Preparation Example 1.

Figure 1:
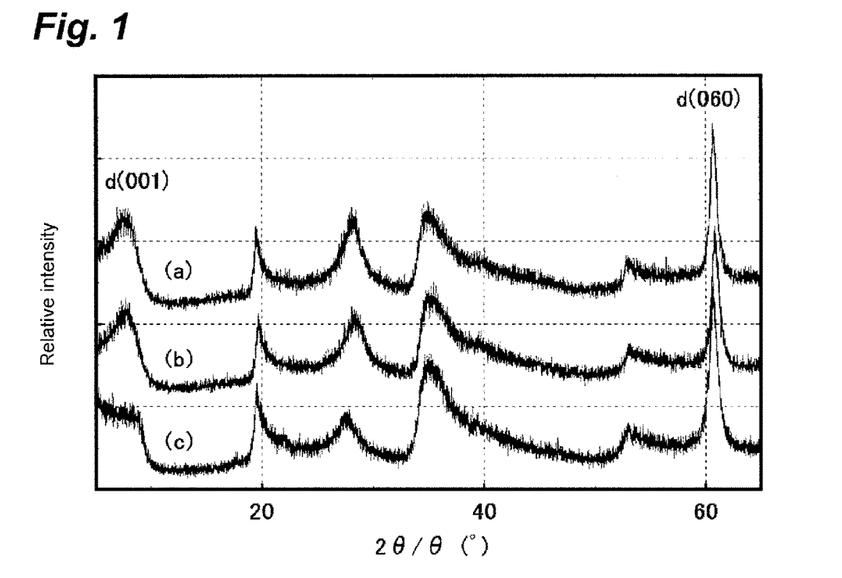
FIG. 1 shows X-ray diffraction patterns of the saponites in Preparation Examples 1 to 3.

FIG. 1 shows analytical results obtained using an X-ray diffractometer (MiniFlex, manufactured by Rigaku Corporation). In FIG. 1, (a) shows an X-ray diffraction pattern of the saponite in Preparation Example 1, (b) shows an X-ray diffraction pattern of the saponite in Preparation Example 2, and (c) shows an X-ray diffraction pattern of the saponite in Preparation Example 3. Presence of a d(001) peak at $2\theta/\theta=7.8°$ to 8.8° shows that each sample is a layered compound having an interlayer distance of 10.0 Å to 11.3 Å. Presence of a d(060) peak at $2\theta/\theta=60.7°$ to 60.9° (1.53 Å) shows that each sample is saponite having 3-octahedral layer structure. Absence of a peak at $2\theta/\theta=39.0°$ shows that each sample contains no free sodium fluoride. Accordingly, saponites in Preparation Example 1 and Preparation Example 2 each are found to have a fluorine atom and a hydroxyl group, and the fluorine atom to be covalently bonded to saponite by isomorphous substitution.

Table 1 shows molar ratios and molar percents of the fluorine atom and the hydroxyl group of each saponite of Preparation Example 1, Preparation Example 2, and Preparation Example 3. The fluorine content means the content of a fluorine atom determined by using an X-ray fluorescence measuring system (RIX 1000, manufactured by Rigaku Corporation). Table 1 shows that saponites in Preparation Example 1 and Preparation Example 2 each contains the fluorine atom at the content of 0.86% by mass and 0.53% by mass, respectively. Furthermore, from the results of X-ray fluorescence analysis, a molar ratio of the fluorine atom and the hydroxyl group in the chemical formula was obtained by calculating a chemical formula of saponite in Preparation Examples according to a method described in "Nendo Handobukku (Clay Handbook), 3rd edition." Moreover, a molar percent obtained by assuming the total molar ratio of the fluorine atom and the hydroxyl group to be 100% is shown in Table 1.

TABLE 1

| | Fluorine content (wt %) | Molar ratio | | Molar percent (%) | |
|---|---|---|---|---|---|
| | | F | OH | F | OH |
| Preparation Example 1 | 0.86 | 0.188 | 1.812 | 9.4 | 90.6 |
| Preparation Example 2 | 0.53 | 0.114 | 1.886 | 5.7 | 94.3 |
| Preparation Example 3 | 0 | 0.000 | 2.000 | 0.0 | 100.0 |

Figure 2:
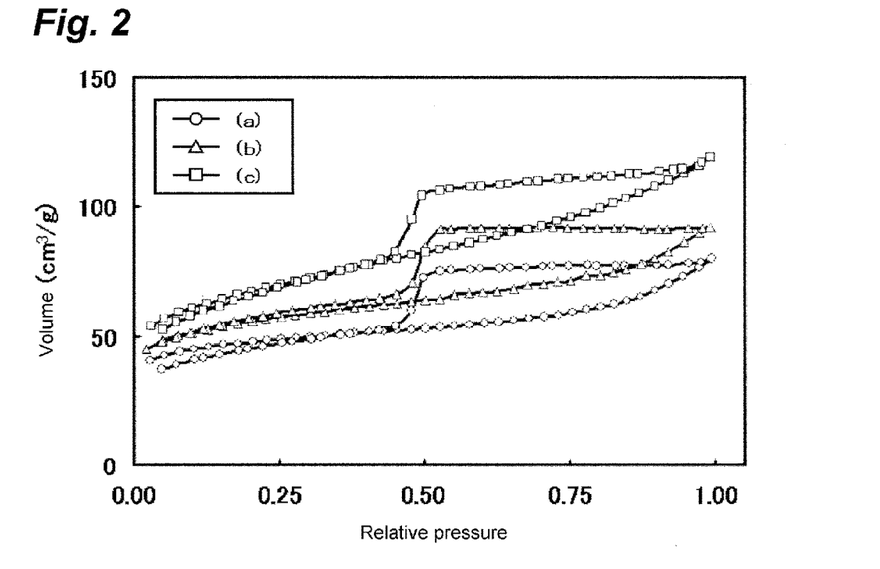
FIG. 2 shows nitrogen adsorption/desorption isotherms of the saponites in Preparation Examples 1 to 3.

FIG. 2 shows nitrogen adsorption/desorption isotherms under conditions of a temperature of liquid nitrogen. In FIG. 2, (a) shows an isotherm of the saponite in Preparation Example 1, (b) shows an isotherm of the saponite in Preparation Example 2, and (c) shows an isotherm of the saponite in Preparation Example 3. The isotherm of each sample has a shape corresponding to Type IV in IUPAC classification to show that each sample is a typical layered compound. An H2 hysteresis loop as seen in the range of from 0.40 to 1.00 of relative pressure shows presence of a mesopore having a diameter of from 2 to 50 nm. The mesopores are considered to originate in a card-house structure of saponite. This card-house structure is formed by irregular stacking of an edge surface and a side surface of a flat nanoparticle.

Table 2 shows analytical results of the cation exchange capacity, the specific surface area, and the surface charge density of the saponites in Preparation Example 1, Preparation Example 2 and Preparation Example 3. The cation exchange capacity was determined based on Schollenberger process using ammonium acetate. The nitrogen adsorption isotherm was determined using a nitrogen adsorption measuring apparatus (AUTOSORB-1, manufactured by Quantachrome Instruments). Moisture of each sample was removed by degassing the sample at 200° C. for 3 hours upon measuring a volume of adsorbed nitrogen (nitrogen adsorption amount). The specific surface area was determined according to Brunauer-Emmett-Teller (BET) process by using data of the adsorbed nitrogen volume in the range of from 0.050 to 0.30 of relative pressure in the nitrogen adsorption isotherm in FIG. 2. The surface charge density was defined as the ratio of the cation exchange capacity to the surface area.

TABLE 2

| | Cation exchange capacity (meq/100 g) | Surface area (m$^2$/g) | Surface charge density (×10$^{-3}$ meq/m$^2$) |
|---|---|---|---|
| Preparation Example 1 | 94.3 | 151.45 | 6.23 |
| Preparation Example 2 | 84.1 | 176.66 | 4.76 |
| Preparation Example 3 | 70.6 | 227.23 | 3.11 |

From the results shown in Table 2, it is found that the cation exchange capacity of each sample increased, and the specific surface area thereof decreased, as the molar percent of the fluorine atom increased. Accordingly, it is found that the surface charge density of each sample increases as the molar percent of the fluorine atom increases. This finding shows that saponite, in which fluorine is subjected to isomorphous substitution, has a strong negative charge and a large surface charge density.

(Example 1) Evaluation of Crystallization Promotion Using Lysozyme

Testing Example 1-1

Thin film-like saponite in Preparation Example 1 was applied to first screening of lysozyme of the white of chicken egg. Crystallization was performed using a lysozyme solution having a predetermined concentration according to a sitting-drop vapor diffusion process.

As a precipitant solution, Crystal Screen I (manufactured by Hampton Research Corporation) being a commercially available screening kit was used. This kit contains fifty kinds of precipitant solutions as shown in Table 3.

As a protein solution, a lysozyme solution in a concentration of 8 mg/mL was prepared by dissolving lysozyme of the white of chicken egg (manufactured by Wako Pure Chemical Industries, Ltd.) into a 0.020 mol/L sodium phosphate buffer solution (pH 7.0) containing 0.150 mol/L of sodium chloride.

TABLE 3

| No. | Salt | | pH buffer | | Precipitant 1 | | Precipitant 2 |
|---|---|---|---|---|---|---|---|
| 1 | Calcium chloride dihydrate | 0.020M | Sodium acetate trihydrate pH 4.6 | 0.10M | 2-Methyl-2,4-pentanediol | 30% v/v | — |
| 2 | — | — | — | — | Potassium sodium tartrate tetrahydrate | 0.40M | — |
| 3 | — | — | — | — | Monoammonium phosphate | 0.40M | — |
| 4 | Trisodium citrate dihydrate | 0.20M | — | — | Ammonium sulfate | 2.0M | — |
| 5 | — | — | Tris(hydroxymethyl)aminomethane-Hydrogen chloride pH 8.5 | 0.10M | 2-Methyl-2,4-pentanediol | 30% v/v | — |
| 6 | Magnesium chloride hexahydrate | 0.20M | Tris(hydroxymethyl)aminomethane-Hydrogen chloride pH 8.5 | 0.10M | Polyethylene glycol 4000 | 30% w/v | — |
| 7 | — | — | Sodium cacodylate trihydrate pH 6.5 | 0.10M | Sodium acetate trihydrate | 1.4M | — |
| 8 | Trisodium citrate dihydrate | 0.20M | Sodium cacodylate trihydrate pH 6.5 | 0.10M | 2-Propanol | 30% v/v | — |
| 9 | Ammonium acetate | 0.20M | Trisodium citrate dihydrate pH 5.6 | 0.10M | Polyethylene glycol 4000 | 30% w/v | — |
| 10 | Ammonium acetate | 0.20M | Sodium acetate trihydrate pH 4.6 | 0.10M | Polyethylene glycol 4000 | 30% w/v | — |
| 11 | — | — | Trisodium citrate dihydrate pH 5.6 | 0.10M | Monoammonium phosphate | 1.0M | — |
| 12 | Magnesium chloride hexahydrate | 0.20M | 4-(2-Hydroxyethyl)piperazine-1-ethanesulfonic acid-Sodium hydroxide pH 7.5 | 0.10M | 2-Propanol | 30% v/v | — |
| 13 | Trisodium citrate dihydrate | 0.20M | Tris(hydroxymethyl)aminomethane-Hydrogen chloride pH 8.5 | 0.10M | Polyethylene glycol 400 | 30% v/v | — |
| 14 | Calcium chloride dihydrate | 0.20M | 4-(2-Hydroxyethyl)piperazine-1-ethanesulfonic acid-Sodium hydroxide pH 7.5 | 0.10M | Polyethylene glycol 400 | 28% v/v | — |
| 15 | Ammonium sulfate | 0.20M | Sodium cacodylate trihydrate pH 6.5 | 0.10M | Polyethylene glycol 8000 | 30% w/v | — |
| 16 | — | — | 4-(2-Hydroxyethyl)piperazine-1-ethanesulfonic acid-Sodium hydroxide pH 7.5 | 0.10M | Lithium sulfate monohydrate | 1.5M | — |
| 17 | Lithium sulfate monohydrate | 0.20M | Tris(hydroxymethyl)aminomethane-Hydrogen chloride pH 8.5 | 0.10M | Polyethylene glycol 4000 | 30% w/v | — |
| 18 | Magnesium acetate tetrahydrate | 0.20M | Sodium cacodylate trihydrate pH 6.5 | 0.10M | Polyethylene glycol 8000 | 30% w/v | — |
| 19 | Ammonium acetate | 0.20M | Tris(hydroxymethyl)aminomethane-Hydrogen chloride pH 8.5 | 0.10M | 2-Propanol | 30% v/v | — |
| 20 | Sodium acetate trihydrate | 0.20M | Sodium acetate trihydrate pH 4.6 | 0.10M | Polyethylene glycol 4000 | 25% w/v | — |
| 21 | Magnesium acetate tetrahydrate | 0.20M | Sodium cacodylate trihydrate pH 6.5 | 0.10M | 2-Methyl-2,4-pentanediol | 30% v/v | — |
| 22 | Sodium acetate trihydrate | 0.20M | Tris(hydroxymethyl)aminomethane-Hydrogen chloride pH 8.5 | 0.10M | Polyethylene glycol 4000 | 30% w/v | — |
| 23 | Magnesium chloride hexahydrate | 0.20M | 4-(2-Hydroxyethyl)piperazine-1-ethanesulfonic acid-Sodium hydroxide pH 7.5 | 0.10M | Polyethylene glycol 400 | 30% v/v | — |
| 24 | Calcium chloride dihydrate | 0.20M | Sodium acetate trihydrate pH 4.6 | 0.10M | 2-Propanol | 20% v/v | — |
| 25 | — | — | Imidazole pH 6.5 | 0.10M | Sodium acetate trihydrate | 1.0M | — |
| 26 | Ammonium acetate | 0.20M | Trisodium citrate dihydrate pH 5.6 | 0.10M | 2-Methyl-2,4-pentanediol | 30% v/v | — |
| 27 | Trisodium citrate dihydrate | 0.20M | 4-(2-Hydroxyethyl)piperazine-1-ethanesulfonic acid-Sodium hydroxide pH 7.5 | 0.10M | 2-Propanol | 20% v/v | — |
| 28 | Sodium acetate trihydrate | 0.20M | Sodium cacodylate trihydrate pH 6.5 | 0.10M | Polyethylene glycol 8000 | 30% w/v | — |
| 29 | — | — | 4-(2-Hydroxyethyl)piperazine-1-ethanesulfonic acid-Sodium hydroxide pH 7.5 | 0.10M | Potassium sodium tartrate tetrahydrate | 0.80M | — |
| 30 | Ammonium sulfate | 0.20M | — | — | Polyethylene glycol 8000 | 30% w/v | — |
| 31 | Ammonium sulfate | 0.20M | — | — | Polyethylene glycol 4000 | 30% w/v | — |
| 32 | — | — | — | — | Ammonium sulfate | 2.0M | — |
| 33 | — | — | — | — | Sodium formate | 4.0M | — |
| 34 | — | — | Sodium acetate trihydrate pH 4.6 | 0.10M | Sodium formate | 2.0M | — |
| 35 | — | — | 4-(2-Hydroxyethyl)piperazine-1-ethanesulfonic acid-Sodium hydroxide pH 7.5 | 0.10M | Monoammonium phosphate monohydrate | 0.80M | Monopotassium phosphate |
| 36 | — | — | Tris(hydroxymethyl)aminomethane-Hydrogen chloride pH 8.5 | 0.10M | Polyethylene glycol 8000 | 8.0% w/v | — |
| 37 | — | — | Sodium acetate trihydrate pH 4.6 | 0.10M | Polyethylene glycol 4000 | 8.0% w/v | — |
| 38 | — | — | 4-(2-Hydroxyethyl)piperazine-1-ethanesulfonic acid-Sodium hydroxide pH 7.5 | 0.10M | Trisodium citrate dihydrate | 1.4M | — |
| 39 | — | — | 4-(2-Hydroxyethyl)piperazine-1-ethanesulfonic acid-Sodium hydroxide pH 7.5 | 0.10M | Polyethylene glycol 400 | 2.0% w/v | Ammonium sulfate |

TABLE 3-continued

| No. | Salt | | pH buffer | | Precipitant 1 | | Precipitant 2 | |
|---|---|---|---|---|---|---|---|---|
| 40 | — | — | Trisodium citrate dihydrate pH 5.6 | 0.10M | 2-Propanol | 20% v/v | Polyethylene glycol 4000 | 20% w/v |
| 41 | — | — | 4-(2-Hydroxyethyl)piperazine-1-ethanesulfonic acid-Sodium hydroxide pH 7.5 | 0.10M | 2-Propanol | 10% v/v | Polyethylene glycol 4000 | 20% w/v |
| 42 | Potassium dihydrogen phosphate | 0.050M | — | — | Polyethylene glycol 8000 | 20% w/v | — | — |
| 43 | — | — | — | — | Polyethylene glycol 1500 | 30% w/v | — | — |
| 44 | — | — | — | — | Magnesium formate dihydrate | 0.20M | — | — |
| 45 | Zinc acetate dihydrate | 0.20M | Sodium cacodylate trihydrate pH 6.5 | 0.10M | Polyethylene glycol 8000 | 18% w/v | — | — |
| 46 | Calcium acetate monohydrate | 0.20M | Sodium cacodylate trihydrate pH 6.5 | 0.10M | Polyethylene glycol 8000 | 18% w/v | — | — |
| 47 | — | — | Sodium acetate trihydrate pH 4.6 | 0.10M | Ammonium sulfate | 2.0M | — | — |
| 48 | — | — | Tris(hydroxymethyl)aminomethane-Hydrogen chloride pH 8.5 | 0.10M | Monoammonium phosphate | 2.0M | — | — |
| 49 | Lithium sulfate | 1.0M | — | — | Polyethylene glycol 8000 | 2.0% w/v | — | — |
| 50 | Lithium sulfate | 0.50M | — | — | Polyethylene glycol 8000 | 15% v/v | — | — |

Saponite in Preparation Example 1 was added to pure water, and thus a 0.2% (w/v) saponite dispersion liquid was prepared. Then, 5 µL of the dispersion liquid was added dropwise onto a micro-bridge (manufactured by Hampton Research Corporation), degassed at room temperature and dried, and thus a thin film of saponite was formed on the micro-bridge.

Upon setting up a sitting-drop, 400 µL of each precipitant solution was added to a well of 24-well plate (manufactured by TPP), and the micro-bridge on which the thin film was formed was put into the well. On the thin film formed on the micro-bridge, 5 µL of the lysozyme solution and 5 µL of the precipitant solution as described in Table 3 were mixed. A high vacuum grease (manufactured by Dow Corning Toray Co., Ltd.) was applied to an inlet of the well, and the well was sealed using a cover glass (manufactured by Matsunami Glass Industries, Ltd.), and allowed to stand for one month at 20±1° C. After being allowed to stand for one month, presence or absence of crystals was investigated by observation using a polarizing microscope (magnification 40 times).

Testing Example 1-2

Testing was performed in the same manner as in Testing Example 1-1, except that the saponite in Preparation Example 2 was used in place of the saponite in Preparation 1.

Comparative Testing Example 1-1

Testing was performed in the same manner as in Testing Example 1-1, except that the saponite in Preparation Example 3 was used in place of the saponite in Preparation 1.

Comparative Testing Example 1-2

Testing was performed in the same manner as in Testing Example 1-1, except that a micro-bridge without applying saponite was prepared and used in which pure water was added dropwise onto the micro-bridge in place of a 0.2% (w/v) saponite dispersion liquid in Testing Example 1-1.

Table 4 shows the results of Testing Example 1-1, Testing Example 1-2, Comparative Testing Example 1-1, and Comparative Testing Example 1-2. The numbers shown in Table 4 indicate the numbers of the solution with crystals among fifty kinds of precipitant solutions used. A success rate of crystallization shows a ratio of solutions with crystals among fifty kinds of precipitant solutions.

TABLE 4

|  | Precipitant solution Nos. with crystals | Success rate of crystallization (%) |
| --- | --- | --- |
| Testing Example 1-1 | 17, 20, 40, 45 | 8.0 |
| Testing Example 1-2 | 15, 17, 21, 29, 45 | 10.0 |
| Comparative Testing Example 1-1 | 17, 22, 45 | 6.0 |
| Comparative Testing Example 1-2 | 30, 34, 45 | 6.0 |

From the results shown in Table 4, it is found that the success rates of crystallization in Testing Example 1-1 and Testing Example 1-2 were larger in comparison with those in Comparative Testing Example 1-1 and Comparative Testing Example 1-2. This finding shows that saponite having the fluorine atom and the hydroxyl group causes an improvement in the success rate of crystallization in searching for lysozyme crystallization conditions.

This phenomenon is considered to be caused by functioning of saponite having the fluorine atom and the hydroxyl group as a field for effectively forming a lysozyme aggregate acting as a crystal nucleus.

In Table 4, according to Testing Example 1-1, crystals are found to be formed in three precipitant solutions (No. 17, No. 20, and No. 40) in which no crystallization was caused in Comparative Testing Example 1-2. In Table 4, according to Testing Example 1-2, crystals are found to be formed in four precipitant solutions (No. 15, No. 17, No. 21, and No. 29) in which no crystallization was caused in Comparative Testing Example 1-2. From these findings, crystallization start conditions that are not discovered in absence of saponite can be discovered by using saponite having the fluorine atom and the hydroxyl group in the first screening. In Table 4, according to Testing Example 1-1, crystals are found to be formed in two precipitant solutions (No. 20 and No. 40) in which no crystallization was caused in Comparative Testing Example 1-1. In Table 4, according to Testing Example 1-2, crystals are found to be formed in three precipitant solutions (No. 15, No. 21, and No. 29) in which no crystallization was caused in Comparative Testing Example 1-1. From these findings, crystallization start conditions that are not discovered in the presence of saponite including no fluorine atom can be discovered by using saponite having the fluorine atom and the hydroxyl group in the first screening.

In addition, in Table 4, according to Testing Example 1-1 and Testing Example 1-2, no crystals are found to be formed in two precipitant solutions (No. 30 and No. 34) in which crystallization was caused in Comparative Testing Example 1-2. These findings are considered to be caused by adsorption of lysozyme as accompanied by addition of saponite to significantly decrease a degree of supersaturation in the drop.

(Example 2) Influence of Saponite on Lysozyme Crystal Growth

Testing Example 2-1

For the purpose of obtaining crystals of lysozyme of the white of chicken egg for X-ray diffraction measurement, the saponite dispersion liquid in Preparation Example 1 was applied. The dispersion liquid contained a cryoprotectant. Crystallization was performed using the lysozyme solution having a predetermined concentration and the dispersion liquid according to a hanging-drop vapor diffusion process.

As the precipitant solution containing the cryoprotectant, a 0.2 mol/L-sodium acetate buffer solution (pH 4.7) containing 1.2 mol/L sodium chloride and 30% (w/v) glycerol was prepared.

As the protein solution, lysozyme of the white of chicken egg (manufactured by Wako Pure Chemical Industries, Ltd.) was dissolved into a 0.020 mol/L-sodium acetate buffer solution (pH 4.7), and thus a 55 mg/mL lysozyme solution was prepared.

A dispersion liquid in which the saponite in Preparation Example 1 was dispersed at a concentration of 0.2% (w/v) was prepared by using the precipitant solution containing the cryoprotectant.

Upon setting up a hanging-drop, 5 µL of the lysozyme solution and 5 µL of the dispersion liquid were mixed on a cover glass subjected to silicone coating treatment (manufactured by Matsunami Glass Industries, Ltd.). To a well of 24-well plate (manufactured by TPP), 400 μL of the cryoprotectant-containing precipitant solution was added. The cover glass was held in an inverted state, and the well was sealed with a high vacuum grease (manufactured by Dow Corning Toray Co., Ltd.), and allowed to stand for one month at 20±1° C.

X-ray diffraction data of lysozyme crystals was collected in the beamline BL6A station at the Photon Factory in the Institute of Materials Structure Science in the High Energy Accelerator Research Organization. From saponite-containing drops, crystals on which saponite was adhered were scooped by using a mounted loop for crystal freezing (Cryoloop, manufactured by Hampton Research Corporation). The crystals were cooled in a nitrogen gas flow at −173° C., and irradiated with synchrotron radiation X-rays having a wavelength of 0.97800 Å. An X-ray diffraction pattern obtained with a CD camera was analyzed using DPS/MOSFLM being a packaged software program.

Testing Example 2-2

Testing was performed in the same manner as in Testing Example 2-1, except that the saponite in Preparation Example 2 was used in place of the saponite in Preparation 1.

Comparative Testing Example 2-1

Testing was performed in the same manner as in Testing Example 2-1, except that the saponite in Preparation Example 3 was used in place of the saponite in Preparation 1.

Comparative Testing Example 2-2

Testing was performed in the same manner as in Testing Example 2-1, except that a precipitant solution to which saponite was not added was used in place of the dispersion liquid in Preparation Example 1 in which saponite was dispersed at a concentration of 0.2% (w/v).

Table 5 shows the results of Testing Example 2-1, Testing Example 2-2, Comparative Testing Example 2-1, and Comparative Testing Example 2-2.

saponite does not affect the space group and the unit-cell parameter of lysozyme crystals. As compared with Comparative Testing Example 2-2, the mosaicity range in Testing Example 2-2 is found to be smaller. Furthermore, the completeness in Testing Example 2-2 is found to be substantially identical with that in Comparative Testing Example 2-2. These results show that the saponite in Testing Example 2-2 does not adversely affect lysozyme crystal growth, and forms high-quality crystals. As described above, even when the agent for searching for crystallization conditions of the present invention is added in a second screening step in searching for crystallization conditions, X-ray diffraction data of protein crystals is found to be obtainable.

(Example 3) Influence of Agent for Searching for Crystallization Conditions in Protein Crystallization from Various Protein Solutions (Dispersion Liquids)

Testing Example 3-1

As an example for searching for conditions of crystallization of each protein in eleven kinds of proteins, the saponite dispersion liquid in Preparation Example 1 was applied. Crystallization was performed using each protein solution and dispersion liquid having a predetermined concentration according to a hanging-drop vapor diffusion process.

Bovine liver catalase, proteinase K derived from *Tritirachium album*, and bovine pancreas trypsin were purchased from Wako Pure Chemical Industries, Ltd. Concanavalin A derived from *Canavalia gladiata*, aprotinin, thaumatin derived from *Thaumatococcus daniellii*, and a human serum albumin were purchased from Sigma-Aldrich Japan K.K. Glucose isomerase derived from *Streptomyces rubiginosus* and xylanase derived from *Trichoderma longibrachiatum* were purchased from Hampton Research Corporation. Avidin of the white of egg was purchased from Nacalai Tesque, Inc. The proteins described above were crystallized without purification. L-Lactate dehydrogenase derived from *Thermus caldophilus* GK24 was expressed by using an *Escherichia coli* expression system and purified according to a prior art literature (Koide S. et al., "Crystallization of Allosteric

TABLE 5

|  | Testing Example 2-1 | Testing Example 2-2 | Comparative Testing Example 2-1 | Comparative Testing Example 2-2 |
|---|---|---|---|---|
| Temperature of crystallization (K) | 293 | 293 | 293 | 293 |
| Temperature of data collection (K) | 100 | 100 | 100 | 100 |
| Space group | $P4_32_12$ | $P4_32_12$ | $P4_32_12$ | $P4_32_12$ |
| Unit-cell parameters (Å) | a = b = 78.365, c = 36.929 | a = b = 78.647, c = 36.903 | a = b = 78.594, c = 36.908 | a = b = 78.498, c = 36.913 |
| Wavelength (Å) | 0.97800 | 0.97800 | 0.97800 | 0.97800 |
| Resolution (Å) | 50.00-1.19 | 50.00-1.19 | 50.00-1.19 | 50.00-1.19 |
| Total number of reflections | 238588 | 234129 | 370989 | 475498 |
| Number of unique reflections | 37470 | 37716 | 37660 | 37625 |
| Mosaicity range | 0.75-1.29 | 0.15-0.17 | 0.38-0.66 | 0.38-0.53 |
| Completeness (%) | 92.2 | 97.3 | 96 | 97.8 |
| R-merge | 0.069 | 0.044 | 0.058 | 0.053 |
| Average I/Sigma (I) | 21.126 | 33.678 | 33.651 | 37.236 |

In any of Testing Examples and Comparative Testing Examples, space groups and unit-cell parameters of formed crystals are found to be identical. This finding shows that the L-Lactate Dehydrogenase from *Thermus caldophilus* and Preliminary Crystallographic Data", The Journal of Biochemistry, 1991, 109, p. 6-7).

Tables 6A, 6B, and 6C show crystallization conditions from each protein solution. Table 6A shows a composition of each protein solution used for crystallization of each protein. Table 6B shows a composition of each precipitant solution used for crystallization of each protein. Table 6C shows a composition of each reservoir solution used for crystallization of each protein.

TABLE 6A

| Protein | protein conc. | pH buffer | |
|---|---|---|---|
| Albumin | 100 mg/mL | 50 mmol/L | Potassium phosphate pH 5.0 |
| Aprotinin | 28 mg/mL | 50 mmol/L | Sodium acetate pH 4.5 |
| Avidin | 9.0 mg/mL | 50 mmol/L | Sodium phosphate pH 5.7 |
| Catalase | 15 mg/mL | 20 mmol/L | Tris(hydroxymethyl)aminomethane-Hydrogen chloride pH 8.5 |
| Concanavalin A | 8.0 mg/mL | 20 mmol/L | Sodium citrate pH 5.8 |
| Glucose isomerase | 15 mg/mL | 20 mmol/L | Tris(hydroxymethyl)aminomethane-Hydrogen chloride pH 7.0 |
| L-Lactate dehydrogenase | 16 mg/mL | 5.0 mmol/L | 4-Morpholinepropane sulfonic acid pH 7.2 |
| Proteinase K | 10 mg/mL | 25 mmol/L | 4-(2-Hydroxyethyl)piperazine-1-ethanesulfonic acid pH 7.0 |
| Thaumatin | 5.0 mg/mL | 20 mmol/L | Piperazine-1,4-bis(2-ethanesulfonic acid) pH 6.8 |
| Trypsin | 15 mg/mL | 25 mmol/L | 4-(2-Hydroxyethyl)piperazine-1-ethanesulfonic acid pH 7.0 |
| Xylanase | 15 mg/mL | 10 mmol/L | N,N-Bis(2-hydroxyethyl)glycine pH 9.0 |

| Protein | Additive 1 | | Additive 2 | |
|---|---|---|---|---|
| Albumin | — | — | — | — |
| Aprotinin | — | — | — | — |
| Avidin | 0.75 mmol/L | Biotin | — | — |
| Catalase | — | — | — | — |
| Concanavalin A | — | — | — | — |
| Glucose isomerase | 1.0 mmol/L | Magnesium chloride | — | — |
| L-Lactate dehydrogenase | 50 mmol/L | Sodium chloride | — | — |
| Proteinase K | 2.0 mmol/L | Phenylmethylsulfonyl fluoride | — | — |
| Thaumatin | — | — | — | — |
| Trypsin | 10 mmol/L | Calcium chloride | 2.5 mg/mL | Benzamidine hydrochloride |
| Xylanase | 1.0 mmol/L | Magnesium sulfate | 1.0 mmol/L | 1,4-Dithiothreitol |

TABLE 6B

| Protein | Precipitant solution conditions pH buffer | |
|---|---|---|
| Albumin | 50 mmol/L | Potassium phosphate pH 5.0 |
| Aprotinin | 50 mmol/L | Sodium acetate pH 4.5 |
| Avidin | 50 mmol/L | Sodium phosphate pH 5.7 |
| Catalase | 100 mmol/L | Tris(hydroxymethyl)aminomethane-Hydrogen chloride pH 8.5 |
| Concanavalin A | 200 mmol/L | Sodium citrate pH 5.8 |
| Glucose isomerase | 100 mmol/L | Tris(hydroxymethyl)aminomethane-Hydrogen chloride pH 7.0 |
| L-Lactate dehydrogenase | 50 mmol/L | 4-Morpholinepropane sulfonic acid pH 7.0 |
| Proteinase K | 100 mmol/L | Tris(hydroxymethyl)aminomethane-Hydrogen chloride pH 8.5 |
| Thaumatin | 200 mmol/L | Piperazine-1,4-bis(2-ethanesulfonic acid) pH 6.8 |
| Trypsin | 25 mmol/L | 4-(2-Hydroxyethyl)piperazine-1-ethanesulfonic acid pH 7.0 |
| Xylanase | 50 mmol/L | N,N-Bis(2-hydroxyethyl)glycine pH 9.0 |

| Protein | Precipitant | | Additive | |
|---|---|---|---|---|
| Albumin | 40% v/v | Polyethylene glycol 400 | 5.0 mmol/L | Sodium azide |
| Aprotinin | 2.8 mol/L | Sodium chloride | — | — |
| Avidin | 3.0 mol/L | Ammonium sulfate | — | — |
| Catalase | 8.0% w/v | Polyethylene glycol 4000 | 300 mmol/L | Lithium chloride |
| Concanavalin A | 1.0 mol/L | Ammonium sulfate | — | — |
| Glucose isomerase | 15% v/v | 2-Methyl-2,4-pentanediol | 200 mmol/L | Magnesium chloride |
| L-Lactate dehydrogenase | 6.0% w/v | Polyethylene glycol 6000 | — | — |
| Proteinase K | 800 mmol/L | Ammonium sulfate | — | — |
| Thaumatin | 600 mmol/L | Potassium sodium tartrate | — | — |
| Trypsin | 20% w/v | Polyethylene glycol 8000 | 200 mmol/L | Ammonium sulfate |
| Xylanase | 250 mmol/L | Ammonium sulfate | 200 mmol/L | Sodium iodide |

TABLE 6C

| Protein | Reservoir solution conditions pH buffer | |
|---|---|---|
| Albumin | 50 mmol/L | Potassium phosphate pH 5.0 |
| Aprotinin | 50 mmol/L | Sodium acetate pH 4.5 |
| Avidin | 50 mmol/L | Sodium phosphate pH 5.7 |
| Catalase | 100 mmol/L | Tris(hydroxymethyl)aminomethane-Hydrogen chloride pH 8.5 |
| Concanavalin A | 200 mmol/L | Sodium citrate pH 5.8 |
| Glucose isomerase | 100 mmol/L | Tris(hydroxymethyl)aminomethane-Hydrogen chloride pH 7.0 |
| L-Lactate dehydrogenase | 50 mmol/L | 4-Morpholinepropane sulfonic acid pH 7.0 |
| Proteinase K | 100 mmol/L | Tris(hydroxymethyl)aminomethane-Hydrogen chloride pH 8.5 |
| Thaumatin | 200 mmol/L | Piperazine-1,4-bis(2-ethanesulfonic acid) pH 6.8 |
| Trypsin | 25 mmol/L | 4-(2-Hydroxyethyl)piperazine-1-ethanesulfonic acid pH 7.0 |
| Xylanase | 50 mmol/L | N,N-Bis(2-hydroxyethyl)glycine pH 9.0 |

| Protein | Reservoir solution conditions | | | |
|---|---|---|---|---|
| | Precipitant | | Additive | |
| Albumin | 40% v/v | Polyethylene glycol 400 | 5.0 mmol/L | Sodium azide |
| Aprotinin | 1.9 mol/L | Sodium chloride | — | — |
| Avidin | 2.75 mol/L | Ammonium sulfate | — | — |
| Catalase | 8.0% w/v | Polyethylene glycol 4000 | 300 mmol/L | Lithium chloride |
| Concanavalin A | 1.0 mol/L | Ammonium sulfate | — | — |
| Glucose isomerase | 15% v/v | 2-Methyl-2,4-pentanediol | 200 mmol/L | Magnesium chloride |
| L-Lactate dehydrogenase | 6.0% w/v | Polyethylene glycol 6000 | — | — |
| Proteinase K | 800 mmol/L | Ammonium sulfate | — | — |
| Thaumatin | 600 mmol/L | Potassium sodium tartrate | — | — |
| Trypsin | 20% w/v | Polyethylene glycol 8000 | 200 mmol/L | Ammonium sulfate |
| Xylanase | 450 mmol/L | Ammonium sulfate | — | — |

Upon crystallization of each protein, each protein solution described in Table 6A, each precipitant solution described in Table 6B, and each reservoir solution described in Table 6C were prepared, respectively.

A dispersion liquid in which the saponite in Preparation Example 1 was dispersed at a concentration of 0.2% (w/v) was prepared by using the precipitant solution.

Upon setting up a hanging-drop, 5 μL of the protein solution and 5 μL of the dispersion liquid were mixed on a cover glass subjected to silicone coating treatment (manufactured by Matsunami Glass Industries, Ltd.). To a well of 24-well plate (manufactured by TPP), 400 μL of the reservoir solution was added. The cover glass was held in an inverted state, and the well was sealed with a high vacuum grease (manufactured by Dow Corning Toray Co., Ltd.), and allowed to stand for two months at 20±1° C.

Formed crystals were evaluated by crystal formation time. The crystal formation time was defined as an elapsed time (days) until first crystals appeared, more specifically, crystals having a size of about 10 μm to 20 μm appeared, under observation using a polarizing microscope (magnification: 40 times).

Testing Example 3-2

Testing was performed in the same manner as in Testing Example 3-1, except that the saponite in Preparation Example 2 was used in place of the saponite in Preparation 1.

Comparative Testing Example 3-1

Testing was performed in the same manner as in Testing Example 3-1, except that the saponite in Preparation Example 3 was used in place of the saponite in Preparation 1.

Comparative Testing Example 3-2

Testing was performed in the same manner as in Testing Example 3-1, except that a precipitant solution to which saponite was not added was used in place of the dispersion liquid in Preparation Example 1 in which saponite was dispersed at a concentration of 0.2% (w/v).

Table 7 shows the crystal formation time from each protein solution in Testing Example 3-1, Testing Example 3-2, Comparative Testing Example 3-1, and Comparative Testing Example 3-2. The numeric value described in Table 7 shows the number of days (unit: day) elapsed until the first crystals were observed. "N.C." described in Table 7 shows that no crystals were formed after the solution was allowed to stand for two months.

TABLE 7

| | Testing Example 3-1 | Testing Example 3-2 | Comparative Testing Example 3-1 | Comparative Testing Example 3-2 |
|---|---|---|---|---|
| Albumin | 14 | 19 | 26 | N. C. |
| Aprotinin | 2 | 7 | 7 | 7 |
| Avidin | 1 | 5 | 5 | 5 |
| Catalase | 5 | 8 | 8 | 12 |
| Concanavalin A | 13 | 20 | 26 | 26 |
| Glucose isomerase | 2 | 2 | N. C. | N. C. |
| L-Lactate dehydrogenase | 5 | 8 | N. C. | N. C. |
| Proteinase K | 8 | N. C. | N. C. | N. C. |
| Thaumatin | 25 | 12 | 28 | 55 |
| Trypsin | 34 | 43 | 42 | N. C. |
| Xylanase | 2 | 9 | 9 | 8 |

In crystallization of each of albumin, glucose isomerase, L-lactate dehydrogenase, and trypsin shown in Table 7, while no crystals are found to be formed in Comparative Testing Example 3-2, crystals are found to be formed in Testing Example 3-1 and Testing Example 3-2. In crystallization of proteinase K shown in Table 7, while no crystals are found to be formed in Comparative Testing Example 3-2, crystals are found to be formed in Testing Example 3-1. In crystallization of aprotinin, avidin, catalase, concanavalin A, thaumatin, and xylanase, as compared with Comparative Testing Example 3-2, the crystal formation time is found to be shortened in Testing Example 3-1 and Testing Example 3-2. These results show that the saponite having the fluorine atom and the hydroxyl group shortens the crystal formation time from each protein solution. Therefore, crystallization start conditions can be modified so as to attain a desired crystal formation time by adding the saponite having the fluorine atom and the hydroxyl group, or changing a fluorine replacement ratio in the saponite to be added in the second screening.

This phenomenon is considered to be caused by functioning of the saponite having the fluorine atom and the hydroxyl group as a field for effectively forming a protein aggregate acting as a crystal nucleus.

In crystallization of each of albumin and trypsin shown in Table 7, while no crystals are found to be formed in Comparative Testing Example 3-2, crystals are found to be formed in Testing Example 3-1. In crystallization of each of catalase and thaumatin, as compared with Comparative Testing Example 3-2, the crystal formation time is found to be shortened in Comparative Testing Example 3-1. These results show that the saponite having the hydroxyl group shortens the crystal formation time from each protein solution.

This phenomenon is considered to be caused by functioning of the saponite having the hydroxyl group as a field for effectively forming a protein aggregate acting as a crystal nucleus.

In crystallization of each of glucose isomerase and L-lactate dehydrogenase shown in Table 7, while no crystals are found to be formed in Comparative Testing Example 3-1, crystals are found to be formed in Testing Example 3-1 and Testing Example 3-2. In crystallization of proteinase K shown in Table 7, while no crystals are found to be formed in Comparative Testing Example 3-1, crystals are found to be formed in Testing Example 3-1. This finding shows that presence of the fluorine atom in the saponite is important for promotion of crystallization of each protein from each protein solution. Therefore, in the second screening, glucose isomerase and L-lactate dehydrogenase can be crystallized in the metastable region by adding the saponite having the fluorine atom and the hydroxyl group.

In crystallization of each protein from each protein solution of albumin, concanavalin A, and thaumatin shown in Table 7, as compared with Comparative Testing Example 3-1, the crystal formation time is found to be significantly shortened in Testing Example 3-1 and Testing Example 3-2. This finding shows that introduction of the fluorine atom by isomorphous substitution causes an improvement in an effect of the saponite having the hydroxyl group on promotion of crystallization.

In crystallization of proteinase K shown in Table 7, while no crystals are found to be formed in Testing Example 3-2, crystals are found to be formed in Testing Example 3-1. This finding shows that a higher content of fluorine atom is suitable for promotion of crystallization of proteinase K. Therefore, in the second screening, proteinase K can be crystallized in the metastable region by adding saponite having a high molar percent of fluorine atom.

In crystallization of thaumatin in Table 7, as compared with Testing Example 3-1, the crystal formation time is found to be shortened in Testing Example 3-2. This finding shows that the molar percent of the fluorine atom to the hydroxyl group in saponite in Preparation Example 2 is suitable for promotion of crystallization of thaumatin.

From the results described above, possibility of crystallization is found to be substantially improved by using the agent for searching for crystallization conditions of the present invention even under solution conditions in which no crystallization is allowed under existing crystallization conditions including the metastable region. Moreover, the agent for searching for crystallization conditions of the present invention promotes a rate of crystallization. However, the present agent does not make crystallization successful only by promotion of the rate, but provides the protein with a field for effectively creating the crystal nucleus, and provides the protein with an effect for allowing crystallization. Furthermore, application of the method for searching for crystallization conditions according to the present invention can be easily anticipated to allow determination of crystallization conditions only by examining conditions in which a load is relatively low.

In addition, all literatures cited in "MODE FOR CARRYING OUT THE INVENTION" are, in relevant part, incorporated herein by reference, but the citation of any literature is not to be considered as an admission that it is prior art with respect to the present invention.

Having described our invention as related to the present embodiments, it is our intention that the invention not be limited by any of the details of the description, unless otherwise specified, but rather be construed broadly within its spirit and scope as set out in the accompanying claims.

This non-provisional application Claims priority under 35 U.S.C. § 119 (a) on Patent Application No. 2011-080944 filed in Japan on Mar. 31, 2011, which is entirely herein incorporated by reference.

The invention claimed is:

1. A method of searching for protein crystallization conditions, comprising:
    searching for protein crystallization conditions with an agent;
    wherein the agent is mixed with a solution in which a protein is dissolved to recover crystallized proteins;
    wherein the agent comprises a water-swellable layered silicate having a fluorine atom and a hydroxyl group;
    wherein the fluorine atom is covalently bonded to the silicate by isomorphous substitution with the hydroxyl group;
    wherein the agent is an agent for controlling protein crystal formation or an agent for promoting protein crystal formation;
    wherein a molar percent of the fluorine atom for a total of the fluorine atom and the hydroxyl group in the layered silicate is from 5% to 15%, and a molar percent of the hydroxyl group for a total of the fluorine atom and the hydroxyl group in the layered silicate is from 85% to 95%; and
    wherein the layered silicate has cation exchange capacity of at least 60 meq/100 g.

2. The method according to claim 1, wherein the molar percent of the fluorine atom for a total of the fluorine atom and the hydroxyl group in the layered silicate is from 5% to 12%, and the molar percent of the hydroxyl group for a total of the fluorine atom and the hydroxyl group in the layered silicate is from 88% to 95%.

3. The method according to claim 1, wherein the layered silicate is smectite, wherein the fluorine atom of the smectite is covalently bonded to the smectite by isomorphous substitution with the hydroxyl group of the smectite.

4. The method according to claim 1, wherein the layered silicate is saponite, wherein the fluorine atom of the saponite is covalently bonded to the saponite by isomorphous substitution with the hydroxyl group of the saponite.

5. The method according to claim 1, wherein the layered silicate has mean particle diameter of from 2 to 50 μm.

6. The method according to claim 1, wherein the layered silicate has specific surface area of from 1 to 1,000 m²/g.

7. The method according to claim 1, wherein the agent is a dispersion liquid agent or a solid agent.

8. The method according to claim 7, wherein the solid agent is a thin film applied on a support.

9. The method according to claim 8, wherein the support is a cover glass, a slide glass, a plate, a bridge, or a rod.

10. The method according to claim 1, wherein the agent is used for searching for conditions of crystallization of a protein in an amount from a nanogram unit to a microgram unit.

11. The method according to claim 1, wherein the agent is used for searching for conditions of crystallization of an expressed protein synthesized according to a gene recombination technology.

12. A method of searching for protein crystallization conditions, which comprises a step of mixing an agent for searching for protein crystallization conditions and a solution in which a protein is dissolved;
  wherein the agent comprises a water-swellable layered silicate having a fluorine atom and a hydroxyl group;
  wherein the fluorine atom is covalently bonded to the silicate by isomorphous substitution with the hydroxyl group;
  wherein a molar percent of the fluorine atom for a total of the fluorine atom and the hydroxyl group in the layered silicate is from 5% to 15%, and a molar percent of the hydroxyl group for a total of the fluorine atom and the hydroxyl group in the layered silicate is from 85% to 95%; and
  wherein the layered silicate has cation exchange capacity of at least 60 meq/100 g.

* * * * *